US00PP32369P2

(12) United States Plant Patent
Kleinwee

(10) Patent No.: US PP32,369 P2
(45) Date of Patent: Oct. 20, 2020

(54) ***OSTEOSPERMUM* PLANT NAMED 'OSTZ0012'**

(50) Latin Name: *Osteospermum ecklonis*
Varietal Denomination: OSTZ0012

(71) Applicant: SYNGENTA CROP PROTECTION AG, Basel (CH)

(72) Inventor: Theodorus Cornelis Maria van Kleinwee, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/602,771

(22) Filed: Dec. 5, 2019

(51) Int. Cl.
*A01H 5/02* (2018.01)
*A01H 6/14* (2018.01)

(52) U.S. Cl.
USPC ..... Plt./360

(58) Field of Classification Search
USPC ..... Plt./360
See application file for complete search history.

*Primary Examiner* — Susan McCormick Ewoldt
(74) *Attorney, Agent, or Firm* — Dale Skalla

(57) ABSTRACT

A new *Osteospermum* plant named 'OSTZ0012' particularly distinguished by the large number of medium sized, rose flowers, is freely branching, has medium vigor and is very floriferous throughout the season.

1 Drawing Sheet

Latin name of the genus and species of the plant claimed: *Osteospermum ecklonis*.

Varietal denomination: 'OSTZ0012'.

BACKGROUND OF THE NEW PLANT

The present invention comprises a new and distinct cultivar of *Osteospermum*, botanically known as *Osteospermum ecklonis* (DC.) Norl., and hereinafter referred to by the cultivar name 'OSTZ0012'.

'OSTZ0012' is a product of a planned breeding program. The new cultivar has a large number of medium sized, rose flowers, is freely branching, has medium vigor and is very floriferous throughout the season.

'OSTZ0012' originated from open pollination made in the summer of 2014 in Enkhuizen, The Netherlands. The female parent was an unpatented, proprietary *Osteospermum* plant designated 'P3160-4', having bigger flowers with a more purple-rose color compared to 'OSTZ0012'.

The male parent of 'OSTZ0012' is unknown as 'OSTZ0012' is the result of an open pollination.

The resulting seeds were sown in January 2015 in Enkhuizen and 'OSTZ0012' was selected as one flowering plant within the progeny of the stated cross in May 2015 in a controlled environment in Enkhuizen, The Netherlands.

The first act of asexual reproduction of 'OSTZ0012' was accomplished when vegetative cuttings were propagated from the initial selection in the summer of 2015 in a controlled environment in Angers, France.

BRIEF SUMMARY OF THE INVENTION

Horticultural examination of plants grown from cuttings of the plant initiated in the summer of 2012 in Angers, France, and continuing thereafter, has demonstrated that the combination of characteristics as herein disclosed for 'OSTZ0012' are firmly fixed and are retained through successive generations of asexual reproduction. 'OSTZ0012' has not been observed under all possible environmental conditions.

The phenotype may vary significantly with variations in environment such as temperature, light intensity and day length.

A Plant Breeder's Right for this cultivar has not yet been applied for. 'OSTZ0012' has not been made publicly available prior to the effective filing date of this application, notwithstanding any disclosure that may have been made less than one year prior to the effective filing date of this application by the inventor or another who obtained 'OSTZ0012' directly from the inventor.

The following traits have been repeatedly observed and are determined to be basic characteristics of the new variety. The combination of these characteristics distinguishes this *Osteospermum* as a new and distinct variety.

DESCRIPTION OF THE PHOTOGRAPHS

Figure 1:
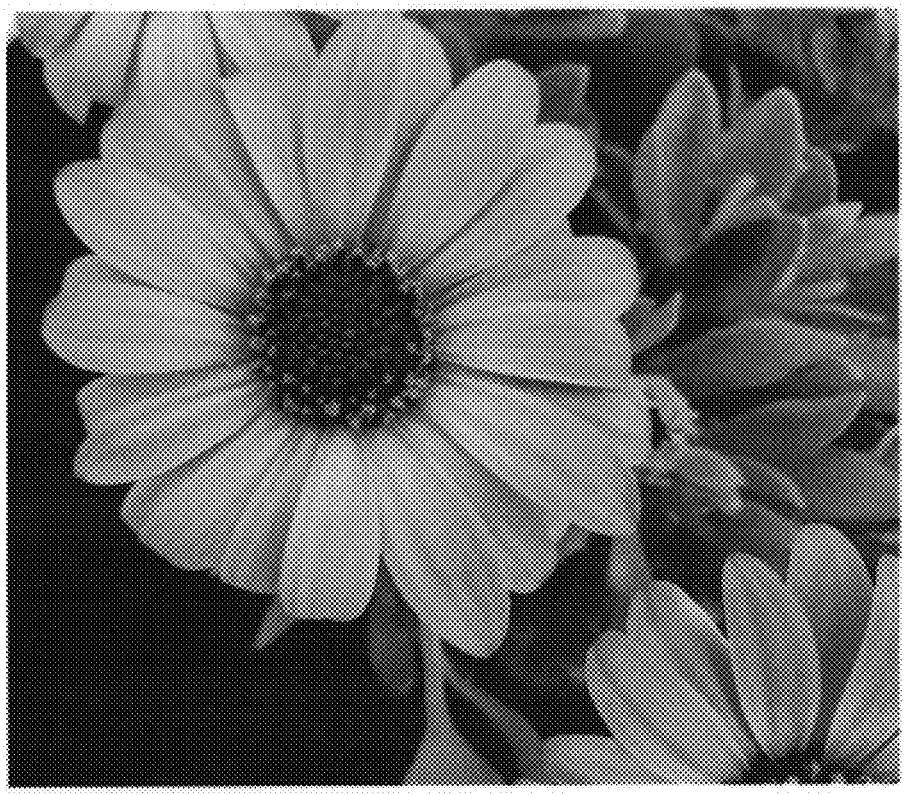
Figure 2:
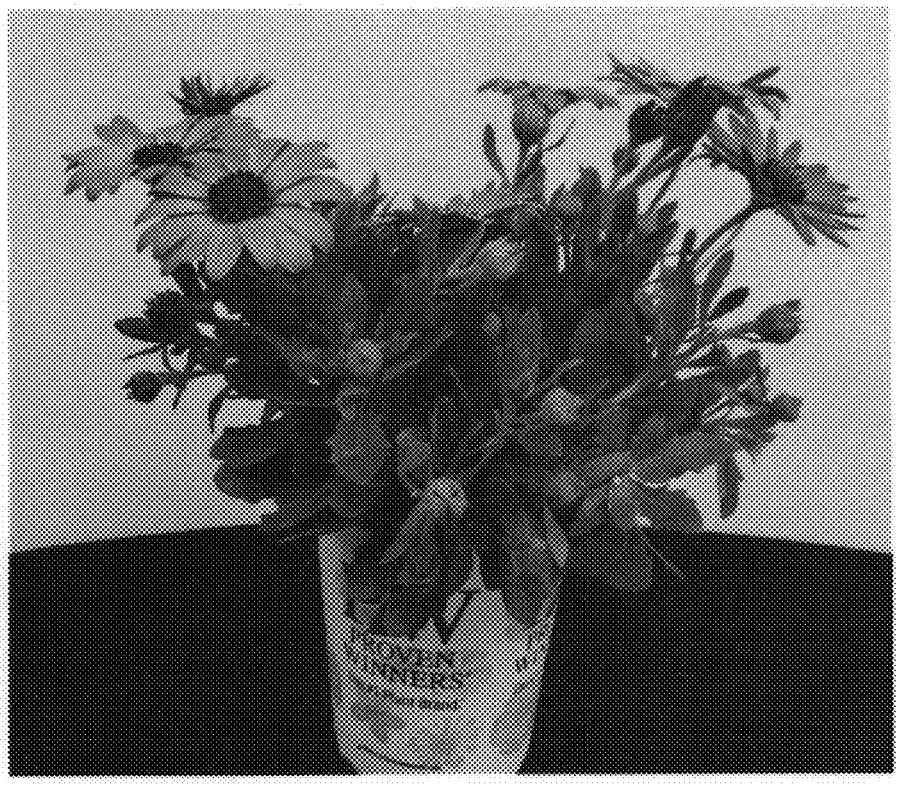

The accompanying photograph drawing shows typical flower and foliage characteristics of 'OSTZ0012' with colors being as true as possible with an illustration of this type. The photograph drawing shows in FIG. 1 a close-up of the flowers, and in FIG. 2 a flowering potted plant of the new variety.

DETAILED BOTANICAL DESCRIPTION

The aforementioned photographs were taken in April 2019 from plants grown in a greenhouse trial in Gilroy, Calif. These plants were grown in 12 cm pots and were approximately 14 weeks of age. The close-up photograph was taken at the same time.

The observations and measurements were taken in Gilroy, Calif. in April 2019 on the same plants.

Color references are made to The Royal Horticultural Society Colour Chart (R.H.S.), 2001.

TABLE 1

DIFFERENCES BETWEEN THE NEW VARIETY 'OSTZ0012' AND A MOST SIMILAR VARIETY

| | 'OSTZ0012' | Tradewinds 'Light purple' (Not patented) |
|---|---|---|
| Flower color: | Rose | Light purple-rose |
| Peduncle length: | long | Very long |
| Receptacle: | Relatively big | Relatively small |

Plant:
*Plant height.*—13 cm.
*Plant height (inflorescence included).*—14-15 cm.
*Plant width.*—15-16 cm.
Foliage:
*Arrangement.*—Alternative, Simple.
*Immature leaf, color upper surface.*—RHS 147A.
*Immature leaf, lower surface.*—RHS 137C.
*Mature, leaf color, upper surface.*—RHS 147A.
*Mature leaf, lower surface.*—RHS 137C.
*Length.*—5.0 cm.
*Width.*—3.0-5.0 cm.
*Shape.*—Oblanceolate.
*Base shape.*—Attenuate.
*Apex shape.*—Acute.
*Margin.*—Entire to slightly spinose.
*Texture, upper surface.*—Smooth, occasionally a short hair.
*Lower surface.*—Very short hair, on margins and veins, only occasionally hairs on rest of lower surface.
*Color of veins, upper surface.*—RHS 144C with a white overtone.
*Color of veins, lower surface.*—RHS 144C with a white overtone.
*Petiole color.*—RHS 144C with a white overtone.
*Length.*—1.5-2.0 cm.
*Diameter.*—4 cm.
*Texture.*—Smooth, but some pubescence at margin.
Stem:
*Quantity of main branches per plant.*—9-10.
*Color of stem.*—RHS 145B, but with brown at base.
*Length of stem.*—12-14 cm.
*Diameter.*—0.5-1.0 cm.
*Length of internodes.*—1.0 cm.
*Texture.*—Glabrous.
*Color of peduncle.*—RHS 143A.
*Length of peduncle.*—Up to 7 cm.
*Peduncle diameter.*—0.2-0.5 cm.
*Texture.*—Light pubescent.
Inflorescence:
*Quantity of inflorescences.*—10.
*Lastingness of individual blooms on the plant.*—10 days.
*Fragrance.*—None.
Bud (just when opening/showing color):
*Color.*—Closest to RHS 80C with stripes.
*Length.*—1.5 cm.
*Width.*—1.5 cm.
*Shape.*—Ovate.
Immature inflorescence:
*Diameter.*—1.5 cm.
*Color of ray florets.*—RHS 53A.
Mature inflorescence:
*Diameter.*—6.5 cm.
*Diameter of disc.*—1.2 cm.
*Average quantity of ray florets.*—22.
*Average quantity of disc florets.*—95.
Ray florets:
*Color upper surface.*—Closest to RHS 80C.
*Color lower surface.*—RHS 186C with RHS 164B.
*Length.*—2.5 cm.
*Width.*—0.7 cm.
*Shape.*—Oblanceolate.
*Apex shape.*—Tridentate.
*Margin.*—Entire.
*Texture, upper surface.*—Glabrous.
*Texture, lower surface.*—Base canescent.
Disc florets:
*Color of florets.*—RHS 177B with purple overtone.
*Length.*—0.5-0.6 cm.
*Width.*—0.2 cm.
*Shape.*—Tubular, elongated.
*Apex shape.*—Acute, 5 pointed.
*Corolla, tube color.*—RHS 79A.
*Length.*—0.2 cm.
*Width.*—0.1 cm.
*Apex shape.*—Acute.
*Base shape.*—Fused, attached petals — jointed corolla lobs.
*Margin.*—Entire.
*Texture.*—Corolla base canescent.
Phyllaries:
*Quantity.*—22.
*Color, upper surface.*—RHS 143A.
*Color, lower surface.*—RHS 143A.
*Length.*—1.0 cm.
*Width.*—0.2 cm.
*Shape.*—Ligulate.
*Apex shape.*—Acute.
*Base.*—Fused.
*Margin.*—Entire.
*Texture.*—Pubescent on both sides.
Reproductive organs:
*Pistil.*—1.
*Length.*—0.1 cm.
*Style color.*—RHS 179A white at base.
*Style length.*—0.7 cm.
*Stigma color.*—RHS 79A.
*Stigma shape.*—Bipartite.
*Stamens.*—Not observed.

What is claimed is:

1. A new and distinct variety of *Osteospermum* plant named 'OSTZ0012' substantially as illustrated and described herein.

* * * * *